(12) United States Patent
Finley et al.

(10) Patent No.: US 10,172,681 B2
(45) Date of Patent: Jan. 8, 2019

(54) SCANNER COVER AND CORRESPONDING SYSTEMS

(71) Applicant: Medline Industries, Inc., Mundelein, IL (US)

(72) Inventors: Christina Finley, Libertyville, IL (US); Michael Turturro, Arlington Heights, IL (US); Timur Selimkhanov, Chicago, IL (US); Derek Roberts, Chicago, IL (US); Sean Kroll, Long Grove, IL (US)

(73) Assignee: Medline Industries, Inc., Northfield, IL (US)

(*) Notice: Subject to any disclaimer, the term of this patent is extended or adjusted under 35 U.S.C. 154(b) by 393 days.

(21) Appl. No.: 15/060,972

(22) Filed: Mar. 4, 2016

(65) Prior Publication Data

US 2017/0252118 A1    Sep. 7, 2017

(51) Int. Cl.
*B65D 85/00* (2006.01)
*A61B 50/00* (2016.01)

(52) U.S. Cl.
CPC .................................. *A61B 50/00* (2016.02)

(58) Field of Classification Search
USPC .... 206/305, 363, 438, 701, 316.1, 521, 591, 206/594
See application file for complete search history.

(56) References Cited

U.S. PATENT DOCUMENTS

| | | | |
|---|---|---|---|
| D225,308 S | 12/1972 | Barefoot | |
| 4,901,852 A | 2/1990 | King | |
| 4,910,819 A | 3/1990 | Brown | |
| D310,969 S | 10/1990 | Butler | |
| D320,562 S | 10/1991 | Brester et al. | |
| D350,268 S | 9/1994 | Grimm | |
| 5,511,702 A * | 4/1996 | Yang | A45F 5/00 206/305 |
| 5,611,429 A * | 3/1997 | Phillips | A61M 5/3205 206/306 |
| D445,678 S | 7/2001 | Malmborg | |
| 6,749,601 B2 * | 6/2004 | Chin | A61B 46/13 206/363 |

(Continued)

OTHER PUBLICATIONS

"Medline Catalog", Exergen Temporal Scanner Thermometers Cap; Medline Catalog; www.medline.com/catalog/catalog.jsp; Unknown Publication date but believed to be prior to present application filing date.

(Continued)

*Primary Examiner* — Jacob K Ackun
(74) *Attorney, Agent, or Firm* — Philip H. Burrus, IV

(57) ABSTRACT

A protective cover (800) for a medical device includes a body (700) and a cap (100) that is selectively attachable to the body. The cap 100 includes an annulus 101 and a rounded vault (102) spanning an interior portion (118) of the annulus. The rounded vault defines a convex exterior (301). A plurality of partial arch trusses (103,104,105,106,107,108, 109) extends from the annulus along the convex exterior toward an apex (601) of the convex exterior. Distal ends (613,614,615,616,617,618,619) of the plurality of partial arch trusses define an interstice (611) at the apex. The partial arch trusses provide longitudinal deflection of impact forces to protect the medical device.

20 Claims, 13 Drawing Sheets

(56) References Cited

U.S. PATENT DOCUMENTS

| | | |
|---|---|---|
| D506,929 S | 7/2005 | Wu |
| D512,913 S | 12/2005 | Gauthier |
| 6,988,664 B1 * | 1/2006 | Lee .................. G06K 7/10881 235/462.45 |
| D562,135 S | 2/2008 | Studee |
| D569,250 S | 5/2008 | Chou |
| 7,529,364 B2 | 5/2009 | Buehler |
| 8,342,323 B2 * | 1/2013 | Shen .................. G01N 21/01 206/305 |
| D675,526 S | 2/2013 | Obrist |
| D678,500 S | 3/2013 | Osepaishvili |
| D679,594 S | 4/2013 | Stull et al. |
| D682,017 S | 5/2013 | Smiedt et al. |
| D684,058 S | 6/2013 | Kwon |
| D704,052 S | 5/2014 | Yoshii et al. |
| D716,143 S | 10/2014 | Schulz et al. |
| D718,127 S | 11/2014 | Moriyama et al. |
| 8,939,287 B2 * | 1/2015 | Markovitch ............ A61L 2/26 206/363 |
| D724,745 S | 3/2015 | Orome et al. |
| D753,998 S | 4/2016 | Murphey et al. |
| D763,696 S | 8/2016 | Eisen |
| D776,533 S | 1/2017 | Kikel |
| D779,951 S | 2/2017 | Servaire |
| 2003/0060807 A1 * | 3/2003 | Tanghoj ............ A61M 25/0017 604/544 |
| 2004/0214130 A1 | 10/2004 | Fischer et al. |
| 2005/0247714 A1 | 11/2005 | Backes et al. |
| 2006/0113208 A1 * | 6/2006 | Clark .................. A61B 46/10 206/438 |
| 2007/0199914 A1 | 8/2007 | Hung |
| 2009/0194531 A1 | 8/2009 | Branco |
| 2013/0220855 A1 * | 8/2013 | Markovitch ............ A61L 2/26 206/363 |
| 2013/0341223 A1 * | 12/2013 | Fong .................. A61B 7/02 206/363 |
| 2016/0066996 A1 * | 3/2016 | Perlman ............... A61B 7/02 206/363 |

OTHER PUBLICATIONS

Vansant, Calvin, "Notice of Allowance", U.S. Appl. No. 29/556,946, filed Mar. 4, 2016; dated May 4, 2017.

* cited by examiner

SCANNER COVER AND CORRESPONDING SYSTEMS

BACKGROUND

Technical Field

This disclosure relates generally to covers for objects, and more particularly to protective covers for electronic devices.

Background Art

Electronic devices are continually becoming more powerful. Microprocessors and other processing circuits continue to become smaller while offering more processing power. Sensors, including magnetic, biometric, thermal, optical, and other sensors, are being manufactured in smaller packages while being able to gather increasingly more data with higher resolutions. Energy storage devices, user interfaces, and other electronic components are becoming more advanced as well.

Unfortunately, these technological advances do not always result in more robust design mechanically. Many electronic devices are still quite susceptible to damage when they are dropped or otherwise strike hard surfaces or objects. When an electronic device strikes an object and breaks, the result is frequently the need to replace the device, which is often a very expensive exercise. This is especially true with medical devices. If a scanner or imaging probe—which is a hand-held device in operation—is dropped, replacing the device may cost thousands of dollars. It would be advantageous to have a cover to prevent the expensive sensors on such medical devices from being damaged, yet without inhibiting ordinary use of the medical device.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

DETAILED DESCRIPTION OF THE DRAWINGS

Figure 1:
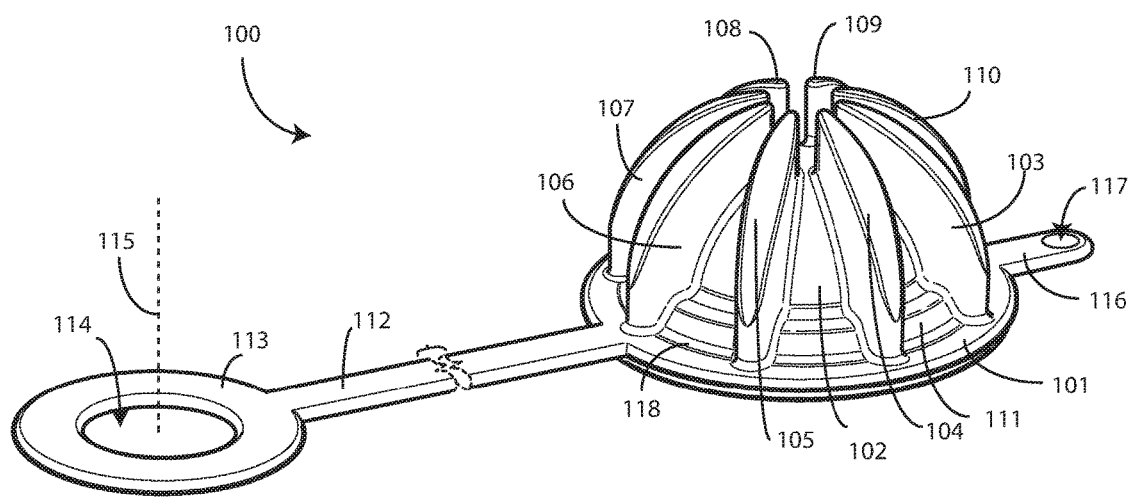
FIG. 1 illustrates a top perspective view of one explanatory cover or cap in accordance with one or more embodiments of the disclosure.

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A. The apparatus components shown below have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Embodiments of the disclosure provide a protective case or covering that fits about an electronic device. In one illustrative embodiment, the protective case or covering is suitable for placement about a medical imaging device, one example of which is a bladder scanner. In one embodiment, the protective case or covering includes recessed areas and openings that are included to ensure that the protective case or covering does not inhibit normal operation of the bladder scanner.

In one or more embodiments, the protective case or covering is manufactured from pliant impact-absorbing material such as a flexible, elastic polymer. The use of a flexible, elastic polymer allows the protective case or covering to be easily installed about the bladder scanner. Additionally, the use of a flexible, elastic polymer facilitates easy removal of the protective case or covering from the bladder scanner for cleaning or replacement. In one or more embodiments, the flexible, elastic polymer is coated with an antimicrobial agent that helps to prevent or limit bacterial growth along the surfaces of the protective case or covering.

In one or more embodiments, the protective case or covering wraps about the bladder scanner to help support joints along the bladder scanner housing. The protective case or covering can include a cap, which is detachable from a body, to expose a scanner sensor. Once a medical services technician is finished using the bladder scanner, they may reattach the cap to the body of the protective case or covering to ensure that the scanner is not damaged by impact that may result from the scanner being dropped.

In one or more embodiments, to prevent the cap from being lost, the cap further includes a tab extending distally from the cap. The tab terminates at an annular disc defining an aperture that is concentrically located along the annular disc in one embodiment. The annular disc can be positioned about a power cord of the scanner so that the cap is not lost when detached from the body.

In one or more embodiments, a cover includes a body and a cap. The body wraps about an electronic device, such as a bladder scanner. The cap is selectively attachable to the body. In one embodiment, the cap comprises an annulus. In one or more embodiments, a rounded vault spans an interior portion of the annulus. In one or more embodiments, the rounded vault defines a convex exterior.

In one or more embodiments, to help cushion a sensitive imaging device, scanner tip, or other critical portion of an electronic device, the cap also includes a plurality of partial arch trusses. In one or more embodiments, each partial arch truss extends from a first end located along the annulus along the convex exterior toward an apex of the convex exterior. Since the vault is a rounded vault, this results in each partial arch truss converging as they extend from the first end to a distal end disposed at a termination point. However, in one or more embodiments each partial arch truss is extends slightly less than would a quarter arch truss. Accordingly, the plurality of distal ends terminates along an apex circle that defines an interstice at the apex of the domed vault. If an electronic device disposed within the cover is dropped on the cap, the partial arch trusses provide longitudinal deflection of impact forces to direct the impact forces along the sides of the cover rather than into the electronic device.

Figure 2:
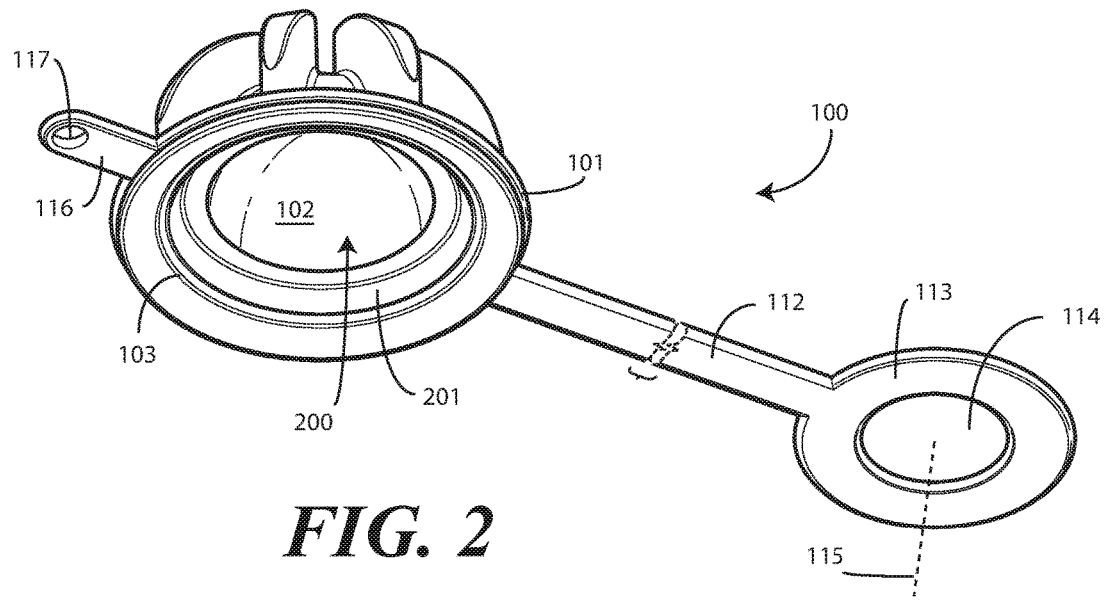
FIG. 2 illustrates a bottom perspective view of one explanatory cover or cap in accordance with one or more embodiments of the disclosure.
Figure 3:
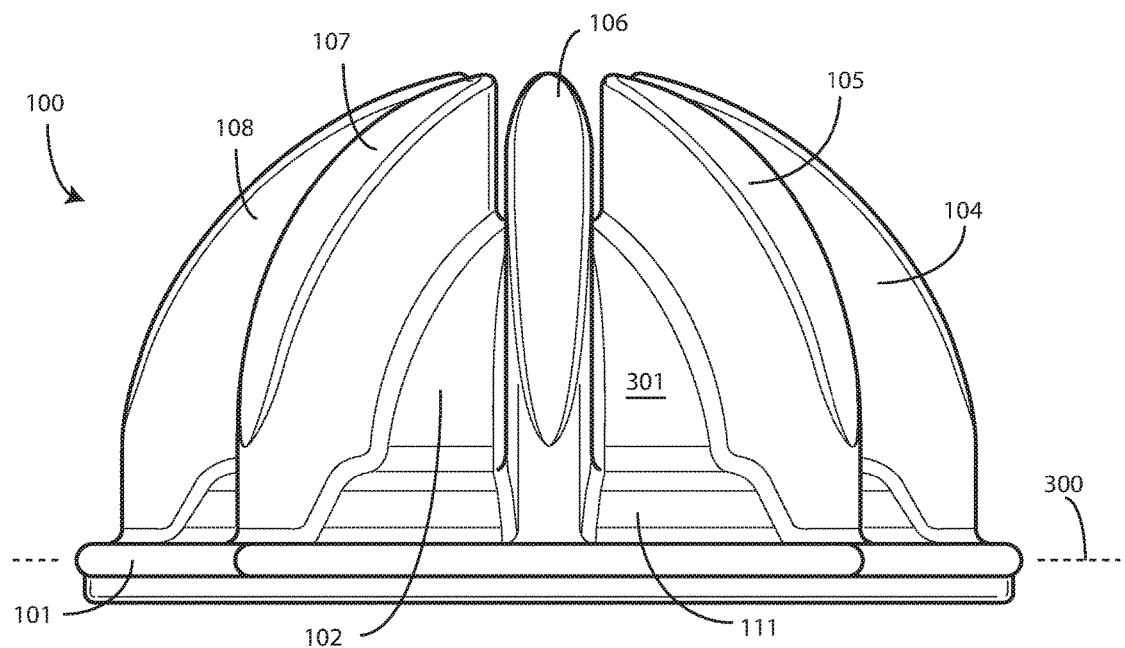
FIG. 3 illustrates a rear elevation view of one explanatory cover or cap in accordance with one or more embodiments of the disclosure.
Figure 4:
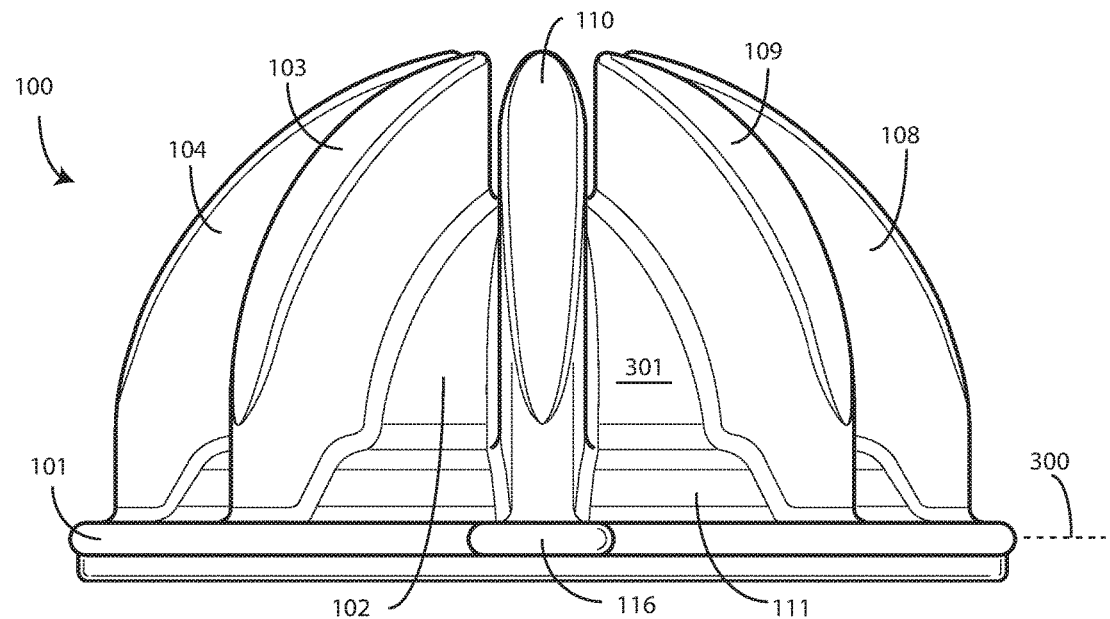
FIG. 4 illustrates a front elevation view of one explanatory cover or cap in accordance with one or more embodiments of the disclosure.
Figure 5:
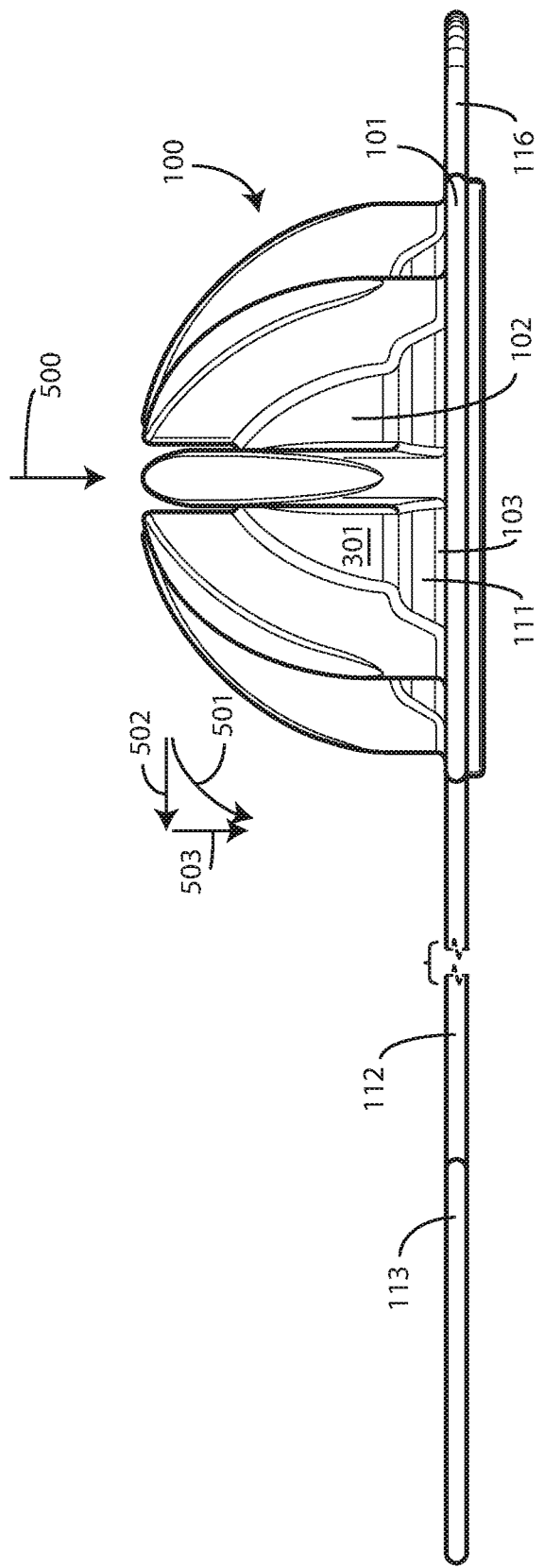
FIG. 5 illustrates a side elevation view of one explanatory cover or cap in accordance with one or more embodiments of the disclosure.
Figure 6:
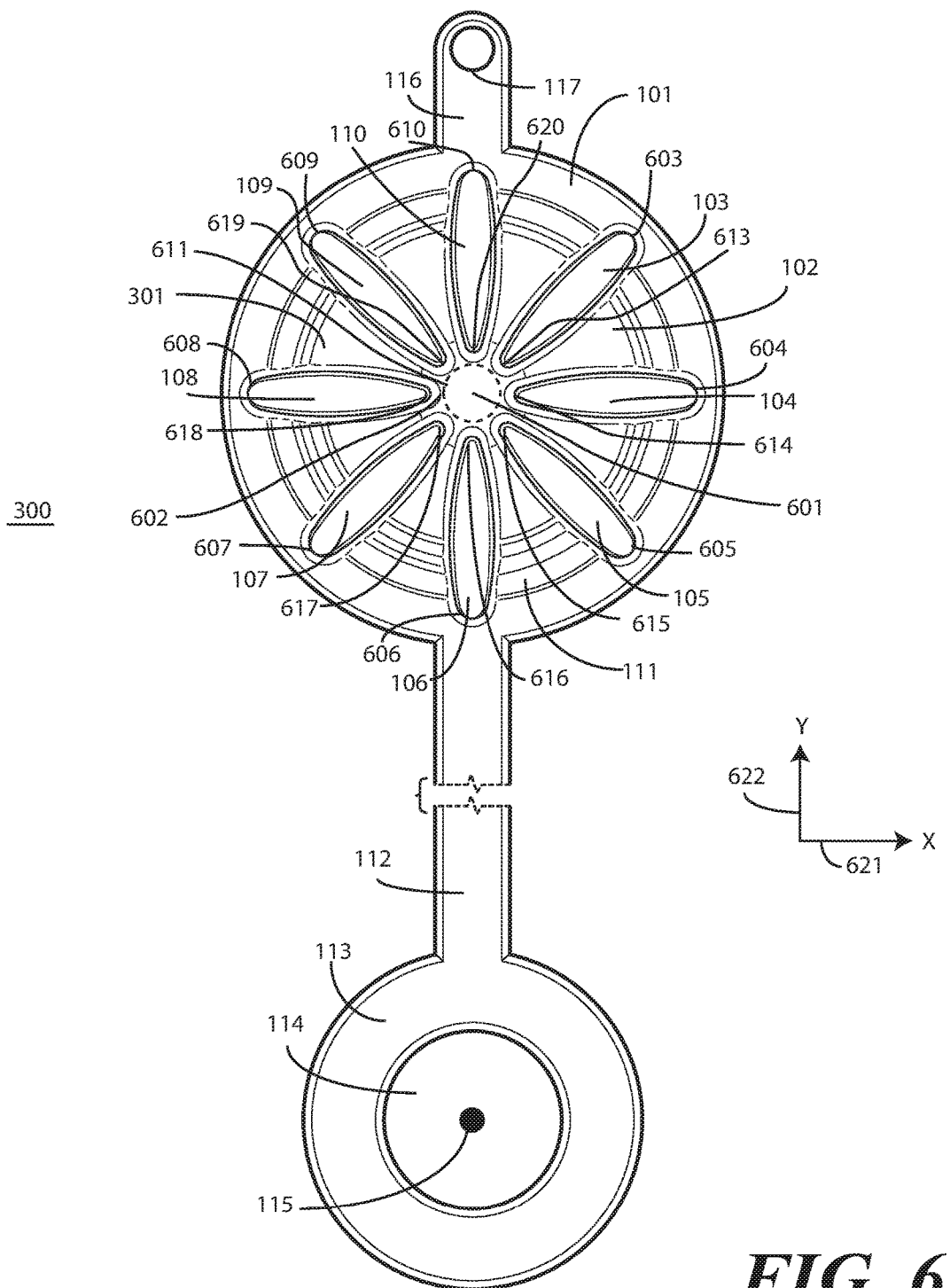
FIG. 6 illustrates a top plan view of one explanatory cover or cap in accordance with one or more embodiments of the disclosure.

Turning now to FIGS. 1-6, illustrated therein is one embodiment of a cap 100 that serves as a cover or cap for a body of a protective cover in accordance with one or more embodiments of the disclosure. FIG. 1 illustrates a top perspective view of the cap 100, while FIG. 2 illustrates a bottom perspective view. FIG. 3 illustrates a rear elevation view of the cap 100, while FIG. 4 illustrates a front elevation view. FIG. 5 illustrates a side elevation view of the cap 100, while FIG. 6 illustrates a top plan view.

In the illustrative embodiment of FIGS. 1-6, the cap includes an annulus 101 defining a plane 300, which is parallel to the page in FIG. 6. As used herein, an "annulus" is a ring-shaped object. The annulus 101 of FIGS. 1-6 surrounds a rounded vault 102 that houses a portion of an electronic device when the cap 100 is coupled to a body to form a cover for the electronic device. Said differently, in this illustrative embodiment the rounded vault 102 spans an interior portion 118 of the annulus 101. Accordingly, the annulus 101 forms a washer-shaped disc extending distally along the plane 300 defined by the annulus in the illustrative embodiment of FIGS. 1-6.

As used herein, a "vault" takes the ordinary English meaning of the term, which is that of a roof or upper covering in the form of an arch or series of partial arches. In this illustrative embodiment, the series of partial arches comprises a plurality of partial arch trusses 103,104,105, 106,107,108,109,110 that extend from the annulus 101 along a convex exterior 301 of the rounded vault 102. As used herein, a "truss" is a framework of struts supporting the roof or upper covering defined by the rounded vault 102. While arches would traditionally be on the interior of a vault, in this illustrative embodiment the plurality of partial arch trusses 103,104,105,106,107,108,109,110 is disposed along the exterior of the rounded vault 102 to provide a framework design to resist compression of the rounded vault 102 should an electronic device to which the cap 100 is attached bet dropped such that the cap 100 strikes a hard surface such as a floor, table, or desk.

In addition to being disposed exterior to the rounded vault 102, in a traditional vault arches would traverse the surface of the vault from one side to the other. However, in this illustrative embodiment each partially arched truss of the plurality of partial arch trusses 103,104,105,106,107,108, 109,110 extends only partially along the convex exterior 301 of the rounded vault 102. As best seen in FIG. 6, in one embodiment each partial arch truss extends from a first end 603,604,605,606,607,608,609,610 disposed at the annulus 101 along the convex exterior 301. Each partial arch truss extends along the convex exterior 301 toward an apex 601 of the convex exterior 301.

In this illustrative embodiment, each partial arch truss extends along the convex exterior 301 to a distal end 613,614,615,616,617,618,619,620 disposed at a termination point 602. In this illustrative embodiment, each partial arch truss has a radius of less than ninety degrees, which makes each partial arch truss less than a quarter arch truss. This results in each distal end 613,614,615,616,617,618,619,620 defining a circle at the apex 601. The circle then defines an interstice 611 at the apex 601 of the convex exterior 301. As used herein, an "interstice" takes the ordinary English meaning of an intervening space disposed between the distal ends 613,614,615,616,617,618,619,620 of the plurality of partial arch trusses 103,104,105,106,107,108,109,110. Said differently, in this illustrative embodiment, the distal ends 613, 614,615,616,617,618,619,620 of the plurality of partial arch trusses 103,104,105,106,107,108,109,110 define an interstice 611 at the apex 601 of the convex exterior 301 of the rounded vault 102.

In one or more embodiments, the cap 100 is manufactured as a unitary, singular component from a pliant impact-absorbing polymer. One example of a pliant impact-absorbing polymer is silicone. For example, in one embodiment the cap 100 is manufactured as a unitary device from sixty-inch durometer silicone. Other materials can be used to make the cap 100 as well. In another embodiment, rubber or polyurethane can be used. Other compressible, flexible, impact-absorbing polymers suitable for use in manufacturing the cap 100 will be obvious to those of ordinary skill in the art having the benefit of this disclosure.

When a pliant impact-absorbing polymer is used to manufacture the cap 100, the plurality of partial arch trusses 103,104,105,106,107,108,109,110 functions as longitudinal force deflectors. Illustrating by example, if an impact force 500 impinges on the apex 601 of the convex exterior 301 of the rounded vault 102, each partial arch truss of the plurality of partial arch trusses 103,104,105,106,107,108,109,110 provides longitudinal deflection 501 of the impact force 500 into an outward force 502 and a downward force 503 to protect sensitive components housed within the rounded vault 102. In one embodiment, the cap 100 is to attach to the roller ball sensor of a bladder scanner. Accordingly, if the bladder scanner is dropped and lands on the top of the cap 100, each partial arch truss of the plurality of partial arch trusses 103,104,105,106,107,108,109,110 provides longitudinal deflection 501 of the impact force 500 about the convex exterior 301 of the rounded vault 102 toward the annulus 101 to protect the sensor of the bladder scanner. This will be shown in more detail with reference to FIG. 11 below.

In one or more embodiments, as best seen in FIG. 6, each partial arch truss of the plurality of partial arch trusses 103,104,105,106,107,108,109,110 defines a teardrop shape due to the fact that the first end 603,604,605,606,607,608, 609,610 of each partial arch truss is wider in cross section than is the distal end 613,614,615,616,617,618,619,620 of the plurality of partial arch trusses 103,104,105,106,107, 108,109,110. Said differently, the first end 603,604,605,606, 607,608,609,610 of each partial arch truss disposed toward at the annulus 101 defines a teardrop base, while the distal end 613,614,615,616,617,618,619,620 defines a teardrop point disposed at the termination point 602. This teardrop shape advantageously helps to further longitudinally deflect any impact force 500 in the x-axis 621 and the y-axis 622 in addition to the longitudinal deflection 501 of the impact force 500 into an outward force 502 and a downward force 503 as described above.

In this illustrative embodiment, the teardrop shape of each partial truss includes convex sides. For example, the sides of each of the plurality of partial arch trusses 103,104,105,106, 107,108,109,110 extending from the first end 603,604,605, 606,607,608,609,610 to the distal end 613,614,615,616,617, 618,619,620 of this illustrative embodiment is convex. However, embodiments of the disclosure are not so limited. In other embodiments, the sides of each of the plurality of partial arch trusses 103,104,105,106,107,108,109,110 extending from the first end 603,604,605,606,607,608,609, 610 to the distal end 613,614,615,616,617,618,619,620 can be concave. In still other embodiments, the sides of each of the plurality of partial arch trusses 103,104,105,106,107, 108,109,110 extending from the first end 603,604,605,606, 607,608,609,610 to the distal end 613,614,615,616,617,618, 619,620 can be straight. Other cross sectional shapes for the plurality of partial arch trusses 103,104,105,106,107,108, 109,110 will be obvious to those of ordinary skill in the art having the benefit of this disclosure.

In one embodiment, the plurality of partial arch trusses 103,104,105,106,107,108,109,110 comprises at least six partial arch trusses. In the illustrative embodiment of FIGS. 1-6, the plurality of partial arch trusses 103,104,105,106, 107,108,109,110 comprises eight partial arch trusses. The number of partial arch trusses can vary based upon application. Illustrating by example, when the perimeter of the base of the rounded vault 102 becomes larger, a larger number of partial arch trusses will be required for sufficient longitudinal deflection 501 of the impact force 500 into an outward force 502 and a downward force 503.

As shown in FIGS. 1-6, in one embodiment each partial arch truss of the plurality of partial arch trusses 103,104, 105,106,107,108,109,110 extends distally away from the convex exterior 301 of the rounded vault 102 by a predetermined height. Where the cap 100 is configured to cover the sensor of a bladder scanner, simulations have demonstrated that a predetermined height of about half an inch are suitable to prevent impact forces 500 from damaging the sensor of the bladder scanner. This predetermined height will vary as a function of the material used to construct the cap 100, the device disposed within the interior 200 of the rounded vault 102, and other factors. Accordingly, other predetermined heights will be obvious to those of ordinary skill in the art having the benefit of this disclosure.

In one or more embodiments, the cap 100 further includes a stair-step protuberance 111. In this illustrative embodiment, the stair-step protuberance 111 is disposed at an intersection of the rounded vault 102 and the annulus 101. The stair-step protuberance 111 can be solid, so as to reinforce the intersection of the rounded vault 102 and the annulus 101 in one embodiment. In another embodiment, as best shown in FIG. 2, the stair-step protuberance 111 defines an orthogonal void 201 to receive an orthogonal protuberance from a bladder scanner.

In one or more embodiments, the cap 100 further comprises a tab 112 extending distally from the annulus 101. In one or more embodiments, the tab 112 extends distally from the annulus 101 along the plane 300 defined by the annulus 101. In one embodiment, the tab 112 comprises a tether that extends distally from the base member that is the annulus 101 along the plane 300 defined by the base member.

In this illustrative embodiment, the tab terminates at an annular disc 113 defining an aperture 114. In one embodiment, the aperture 114 is concentrically located with the annular disc 113 along a central axis 115. In one embodiment, the annular disc 113 defines an engagement loop disposed at a distal end of the tether. As will be described in more detail below, when an electronic device such as a bladder scanner is disposed within a cover that includes the cap 100, a power cord can be threaded through the aperture 114 so that the cap 100 does not become lost when removed from the bladder scanner.

In one or more embodiments, the cap 100 further comprises a body coupler 116. In this illustrative embodiment, the body coupler 116 extends distally from the annulus 101 along the plane 300 defined by the annulus 101. In one embodiment, the body coupler 116 extends distally from the annulus 101 on a side of the annulus 101 opposite the tab 112. Said differently, in this illustrative embodiment, the body coupler 116 is 180 degrees out of phase from the tab 112 about the annulus 101.

Figure 15:
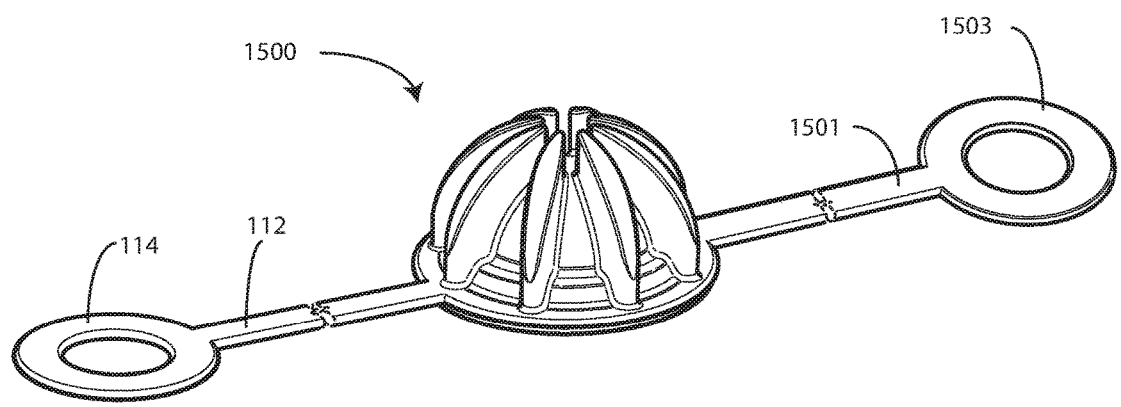
FIG. 15 illustrates another explanatory cover in accordance with one or more embodiments of the disclosure.

In one or more embodiments, the body coupler 116 can be replaced by a second tab terminating at a second disc. Turning briefly to FIG. 15, illustrated therein is an alternate cape 1500 that includes the tab 112 and a second tab 1501 terminating at a second annular disc 1503. When an electronic device such as a bladder scanner is disposed within a cover that includes the cap 1500, a power cord can be threaded through both the annular disc 113 and the second annular disc 1503 so the cap remains securely coupled to the electronic device.

Turning now back to FIGS. 1-6, In one or more embodiments, the body coupler 116 defines an aperture 117. As will be shown in more detail below, in one or more embodiments a second part of a cover defined by a body includes a boss to retain the cap 100 in an attached configuration to the body. In one embodiment the boss frictionally engages the aperture 117 to retain the cap 100 in the attached configuration. This will be shown in more detail below with reference to FIG. 11.

Figure 7:
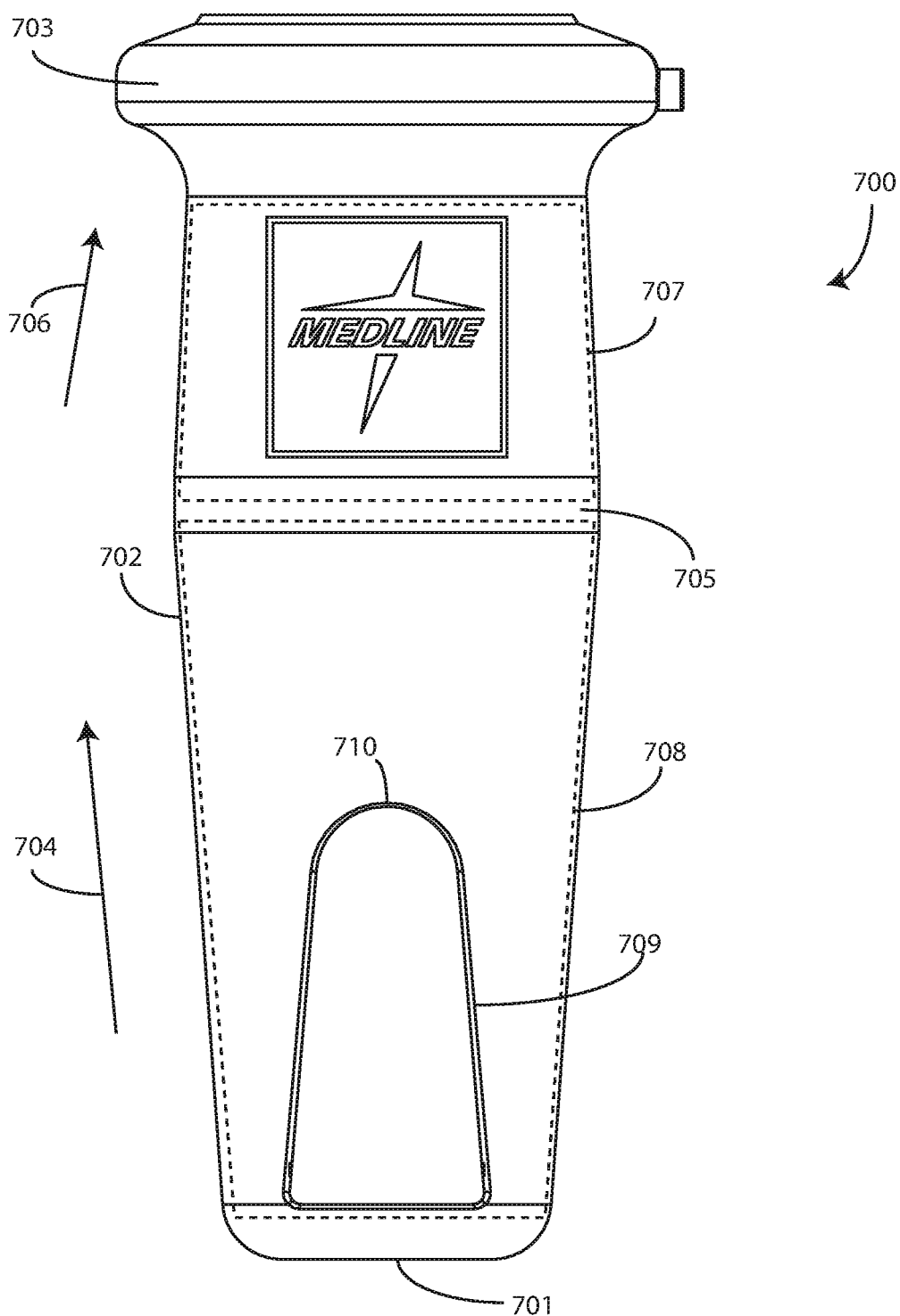
FIG. 7 illustrates one explanatory body of a cover in accordance with one or more embodiments of the disclosure.

Turning now to FIG. 7, illustrated therein is one explanatory body 700 of a cover, suitable for use with the cap (100) of FIGS. 1-6 in accordance with one or more embodiments of the disclosure. In this illustrative embodiment, the body 700 includes a base member 701 and a round sidewall 702. In one embodiment, the round sidewall 702 extends distally from the base member 701 to a girdle 703. The body 700 is defined by a body height 805.

In one embodiment, the round sidewall 702 is not straight. As shown in FIG. 7, in one illustrative embodiment the round sidewall 702 initially extends outward 704 from the base member 701 to a waist 705. The round sidewall 702 then extends inward 706 from the waist 705 to the girdle 703. In so doing, the round sidewall 702 defines a double-opposing frustoconical housing, with the base of a shape of a first frustum 707 abutting the base of an inverted second frustum 708 at the waist 705. While this is one explanatory shape for the round sidewall 702, embodiments of the disclosure are not so limited. In other embodiments, the round sidewall 702 can be straight, convex, or concave. Other shapes suitable for the round sidewall 702 will be obvious to those of ordinary skill in the art having the benefit of this disclosure.

In the illustrative embodiment of FIG. 7, the round sidewall 702 defines an opening 709. As noted above, in one or more embodiments the body 700 is configured to encapsulate the housing of a bladder scanner. Accordingly, in one or more embodiments the opening 709 is included to allow exposure of a control panel of the bladder scanner through the round sidewall 702. In this illustrative embodiment, the opening 709 is an arched opening defined by an upper arch 710. Other shapes of other openings will be obvious to those of ordinary skill in the art having the benefit of this disclosure.

In one or more embodiments, the round sidewall 702 defines a concave engagement region 711 between the waist 705 and the girdle 703. When the body 700 is used with a bladder scanner, the concave engagement region 711 can provide a comfortable place for a user to place their hand when using the bladder scanner.

As with the cap (100), in one or more embodiments the body 700 is manufactured as a unitary, singular component from a pliant impact-absorbing polymer such as silicone or polyurethane. In one embodiment, the body 700 is manufactured from 60A durometer silicone. Other materials can be used as well. Numerous other compressible, flexible, impact-absorbing polymers suitable for use in manufacturing the body 700 will be obvious to those of ordinary skill in the art having the benefit of this disclosure.

Figure 8:
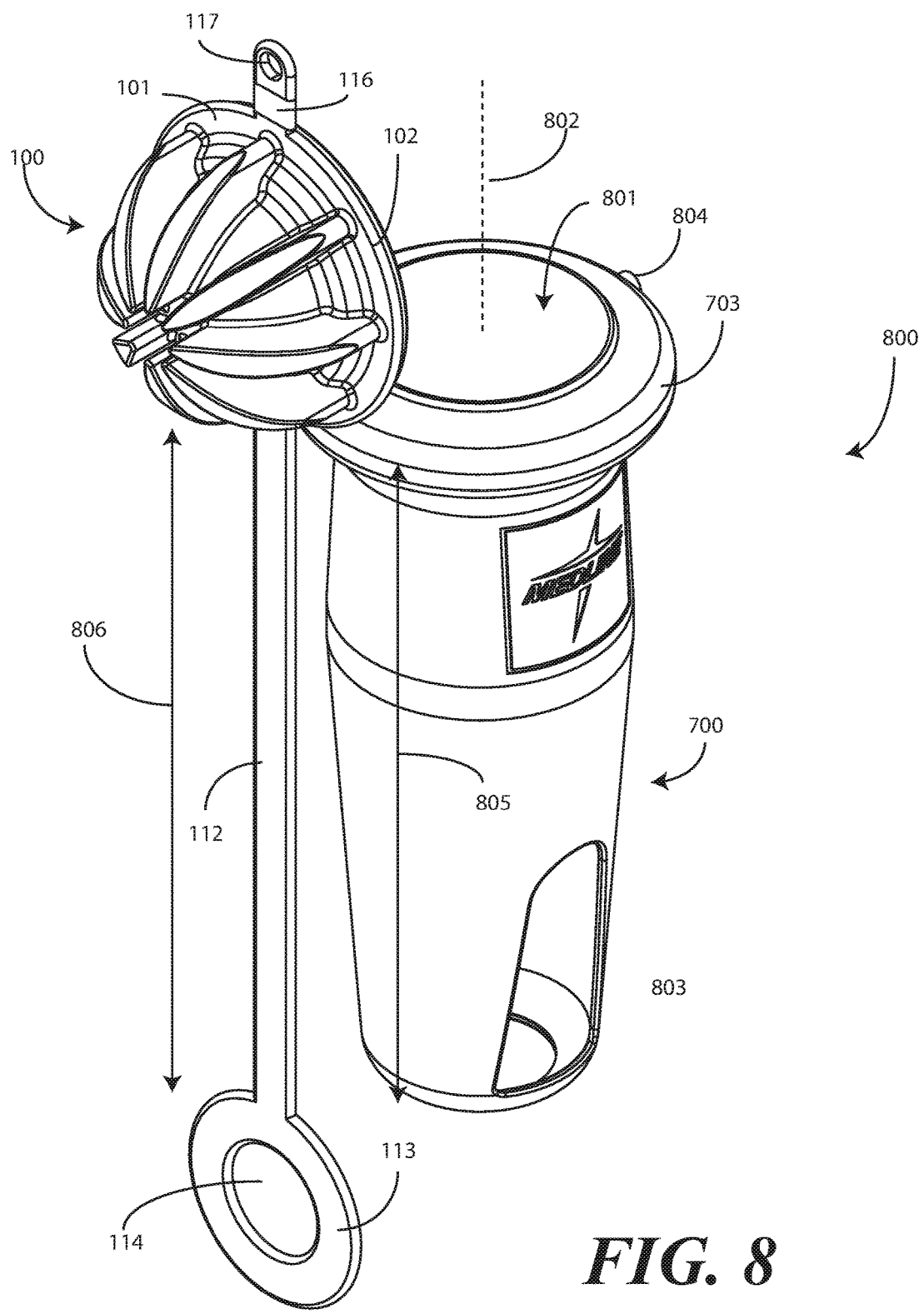
FIG. 8 illustrates one explanatory cover in accordance with one or more embodiments of the disclosure.

Turning now to FIG. 8, illustrated therein is an explanatory protective cover 800 for an electronic device configured in accordance with one or more embodiments of the disclosure. The protective cover 800 includes the cap 100 of FIGS. 1-6 and the body 700 of FIG. 7.

As shown from the perspective view of FIG. 8, in one or more embodiments the girdle 703 of the body 700 defines an aperture 801 to receive a medical device such as a bladder scanner. In one embodiment, the aperture 801 is concentrically aligned with a central axis 802 of the body 700.

In one or more embodiments, the base member 701 of the body 700 defines a second aperture 803. In one embodiment, the second aperture 803 is also concentrically aligned with a central axis 802 of the body 700. When a medical device, such as a bladder scanner, is placed within the body 700, the inclusion of the second aperture 803 allows a power cord to extend through the base member 701 out of the body 700. This will be shown in more detail with reference to FIG. 13 below.

In one or more embodiments, the body 700 defines a boss 804 that extends distally from the girdle 703. As noted above, the cap 100 can include a body coupler 116 defining an aperture 117. When the rounded vault 102 of the cap 100 is placed atop the girdle 703 so as to cover the aperture 801 at the top of the body 700, a first side of the annulus 101 can be retained against the girdle 703 by folding the body coupler 116 about the exterior of the girdle 703 so that the boss 804 can engage the aperture 117 to latch the cap 100 to the body 700.

As shown in FIG. 8, in one or more embodiments the tab 112 of the cap 100 extends distally from the annulus 101 by a distance 806 that is greater than the body height 805 of the body 700. Where this is the case, the annular disc 113 can be used to retain the side of the annulus 101 opposite the body coupler 116 to the girdle 703. Recall from above that in one embodiment when a medical device such as a bladder scanner is placed within the body 700 a power cord can extend outwardly from the second aperture 803 through the base member 701 out of the body 700. This power cord can be laced through the aperture 114 of the annular disc 113. Where the tab 112 of the cap 100 extends distally from the annulus 101 by a distance 806 that is greater than the body height 805 by an amount to hold the tab 112 taught when the boss 804 engages the aperture 117 to latch the cap 100 to the body 700, this tension functions to retain the rounded vault 102 atop the girdle 703 and covering the aperture 801. Illustrating by example, in one embodiment suitable for a bladder scanner the body height is about 158 millimeters. A distance 806 running from the edge of the annulus 101 to the center of the aperture 114 in the annular disc 113 is then about 170 millimeters. This difference in length, i.e., about 12 millimeters, allows the tab 112 to retain the rounded vault 102 atop the girdle 703 and covering the aperture 801 when the boss 804 engages the aperture 117 to latch the cap 100 to the body 700. While other applications will include different lengths and body heights, the ratio of heights will remain roughly the same.

Figure 9:
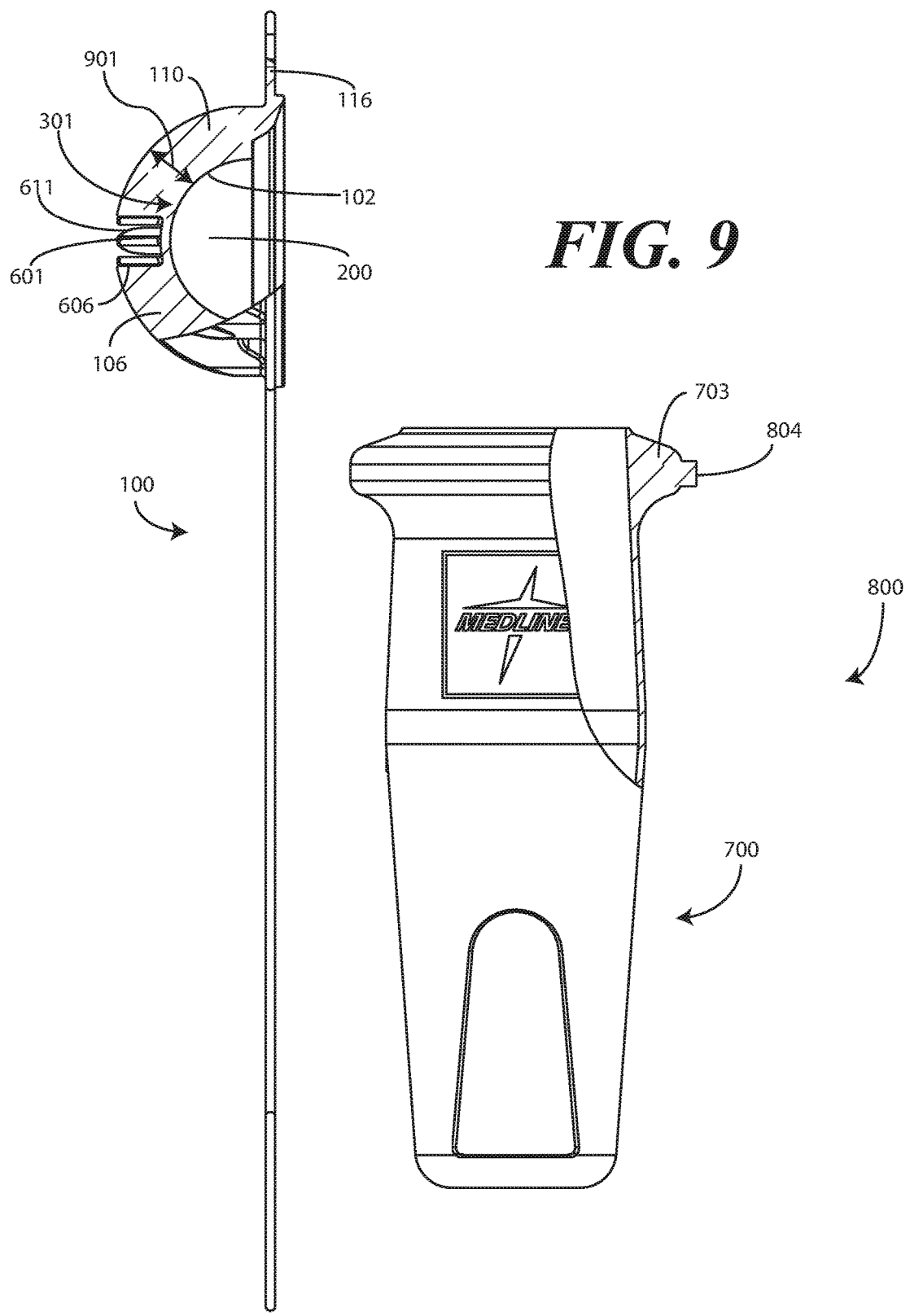
FIG. 9 illustrates sectional views of one explanatory cover in accordance with one or more embodiments of the disclosure.

Turning now to FIG. 9, illustrated therein is a sectional view of one explanatory protective cover 800 for an electronic device configured in accordance with one or more embodiments of the disclosure. The protective cover 800 includes the cap 100 of FIGS. 1-6 and the body 700 of FIG. 7. In this sectional view, cross sections of the boss 804, the girdle 703, the rounded vault 102, the body coupler 116, and two of the partial arch trusses 106,110 can be seen.

As noted above, in one embodiment each partial arch truss 106,110 extends distally away from the convex exterior 301 of the rounded vault 102 by a predetermined height 901. In one or more embodiments, this predetermined height 901 is about one half of an inch. This predetermined height 901, when the cap 100 is manufactured from 60A durometer silicone is suitable to prevent impact forces (500) from damaging the sensor of the bladder scanner disposed within the body 700. However, this predetermined height 901 will vary as a function of the material used to construct the cap 100, the device disposed within the interior 200 of the rounded vault 102, and other factors. Accordingly, other predetermined heights will be obvious to those of ordinary skill in the art having the benefit of this disclosure.

The sectional view of the cap 100 shown in FIG. 9 also includes a more detailed view of the interstice 611 disposed at the apex 601 of the rounded vault 102 between the distal ends 616,620 of the partial arch trusses 106,110. The inclusion of the interstice 611 advantageously prevents impact forces (500) from being directed into the apex 601 of the rounded vault 102. Instead, they are shed outwardly and down, into and out of the page, due to the construction of the partial arch trusses 106,110 noted above. When a sensor of a bladder scanner or other medical device is disposed within the interior 200 of the rounded vault 102, it will be protected by the cap 100 when dropped on the floor or other hard surfaces.

Figure 10:
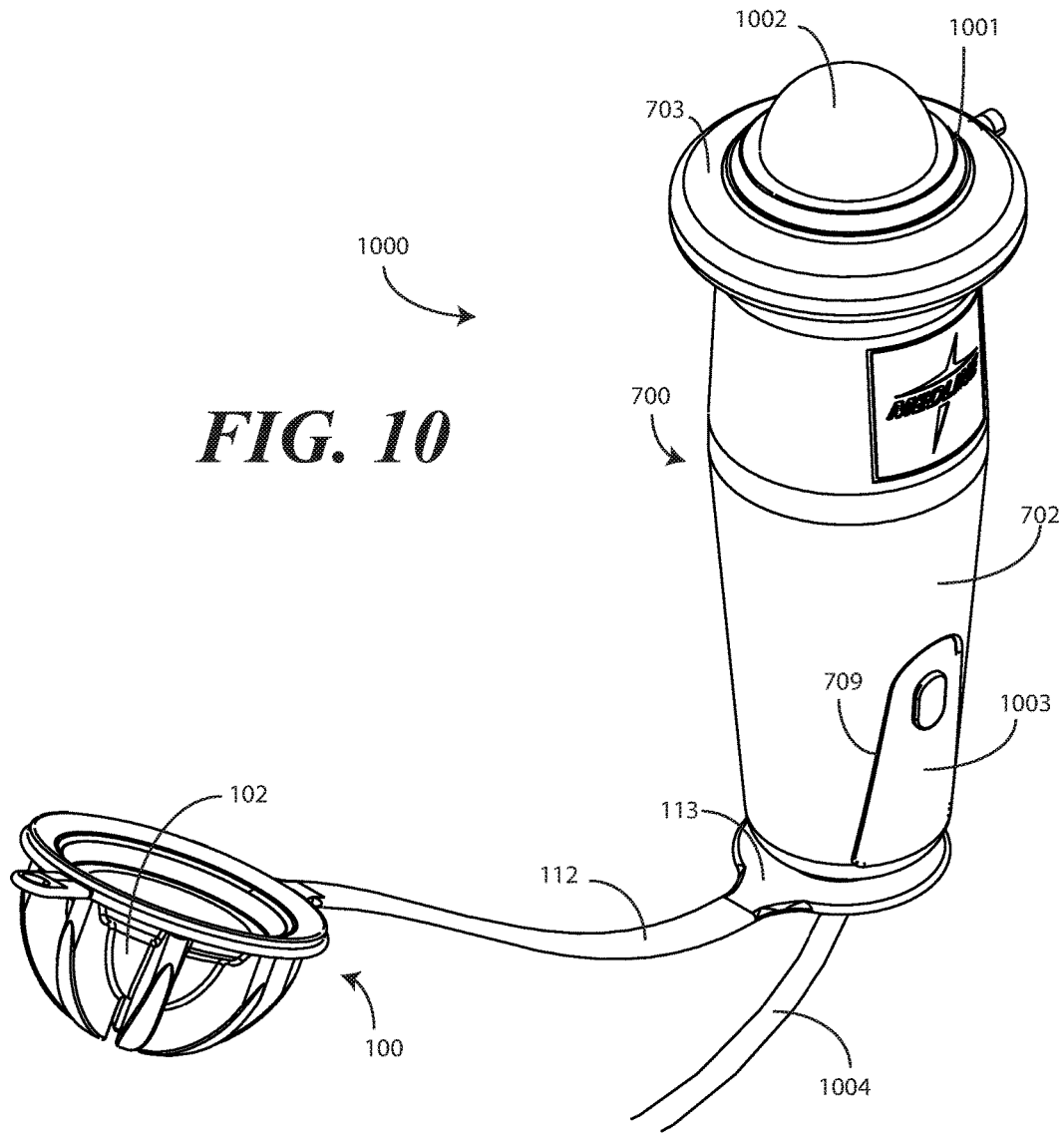
FIG. 10 illustrates one explanatory cover covering a medical device, with a cap in an open configuration, in accordance with one or more embodiments of the disclosure.

Turning now to FIG. 10, illustrated therein is a bladder scanner system 1000 in accordance with one or more embodiments of the disclosure. As shown in FIG. 10, a bladder scanner 1001 has been inserted into the body 700 of a protective cover (800). The sensor 1002 extends outwardly through the aperture (801) in the girdle 703. The control panel 1003 of the bladder scanner 1001 is exposed through the opening 709 disposed in the rounded sidewall 702 of the body 700.

As shown in FIG. 10, in one or more embodiments a power cord 1004 extends outwardly from the second aperture (803) through the base member 701 out of the body 700. In this illustrative embodiment, the power cord 1004 passes through the aperture (114) of the annular disc 113. Accordingly, when the bladder scanner 1001 is in use, and the rounded vault 102 of the cap 100 is removed from the sensor 1002 of the bladder scanner 1001, it will be retained by the tab 112 to the power cord 1004. Advantageously, this configuration allows the bladder scanner 1001 to be used as shown in FIG. 12 by holding the body 700 without the cap 100 attached while, at the same time, preventing the cap from being dropped and contaminated or, worse, lost. Once a medical services provider is done using the bladder scanner 1001, they simply place the rounded vault 102 atop the sensor 1002 of the bladder scanner 1001. This configuration is shown in FIG. 11.

Figure 11:
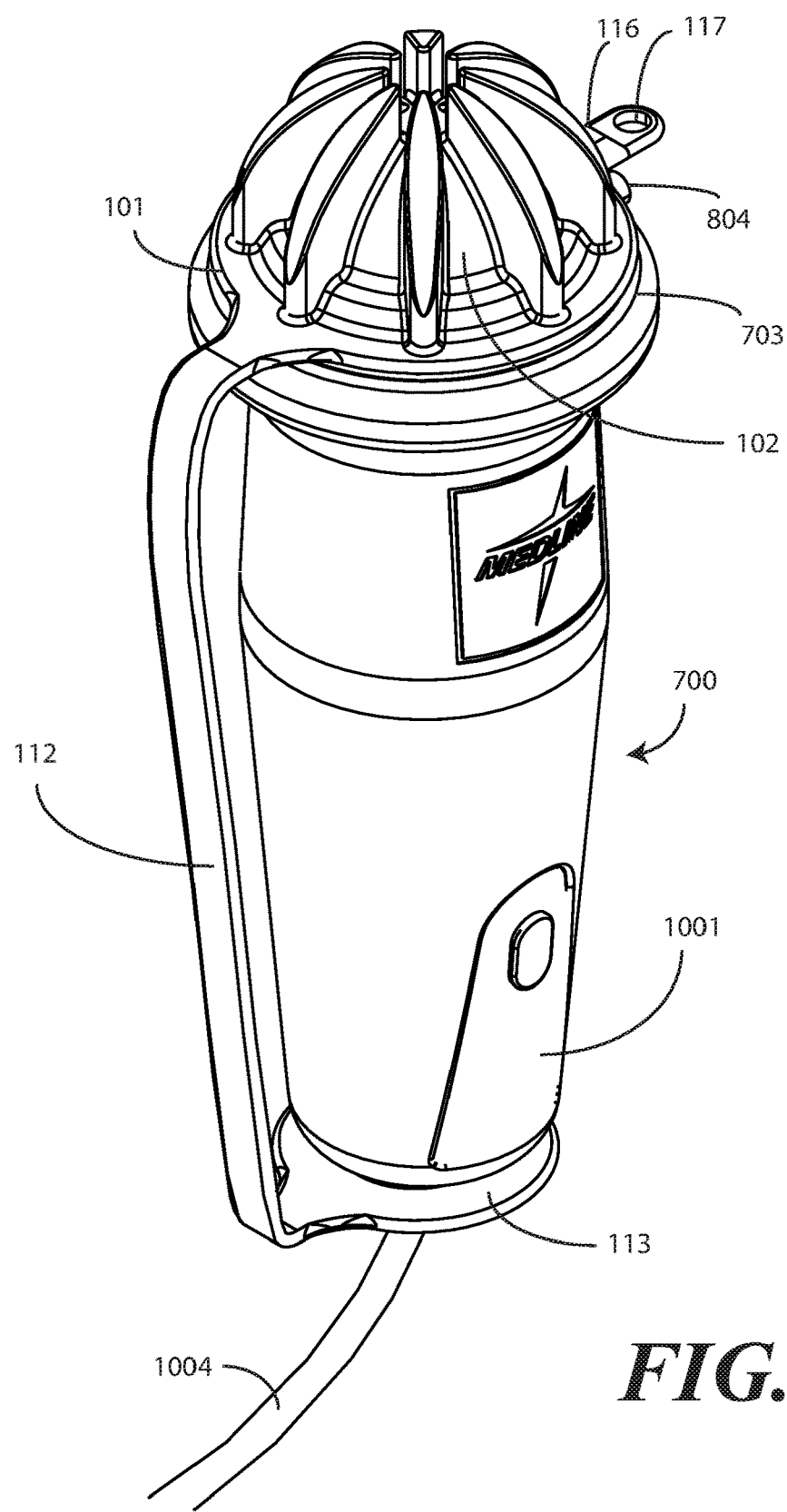
FIG. 11 illustrates one explanatory cover covering a medical device, with the cap in an attached configuration, in accordance with one or more embodiments of the disclosure.
Figure 12:
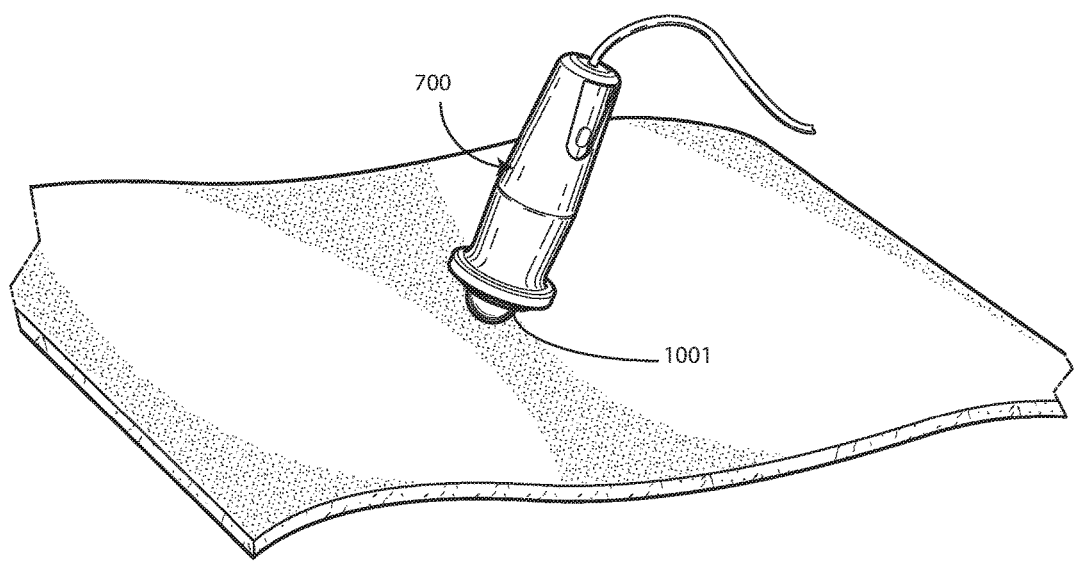
FIG. 12 illustrates an explanatory device in use when covered by one explanatory cover in accordance with one or more embodiments of the disclosure.

Turning now to FIG. 11, to keep the rounded vault 102 securely attached to the body 700 and covering the sensor (1002) of the bladder scanner 1001, one simply folds the body coupler 116 about the exterior side of the girdle 703 to latch the aperture 117 about the boss 804 extending from the girdle 703. The tab 112 is retained taught on the opposite side due to the fact that the power cord 1004 extends through the aperture (114) of the annular disc 113, thereby securing the annulus 101 to the girdle 703 and the rounded vault 102 atop the sensor (1002) of the bladder scanner 1001.

As shown in FIG. 11, in one illustrative embodiment, the girdle 703 has a width that is greater than the diameter of the annulus 101. This configuration helps to ensure a mechanically stable coupling between the girdle and the annulus 101.

Figure 13:
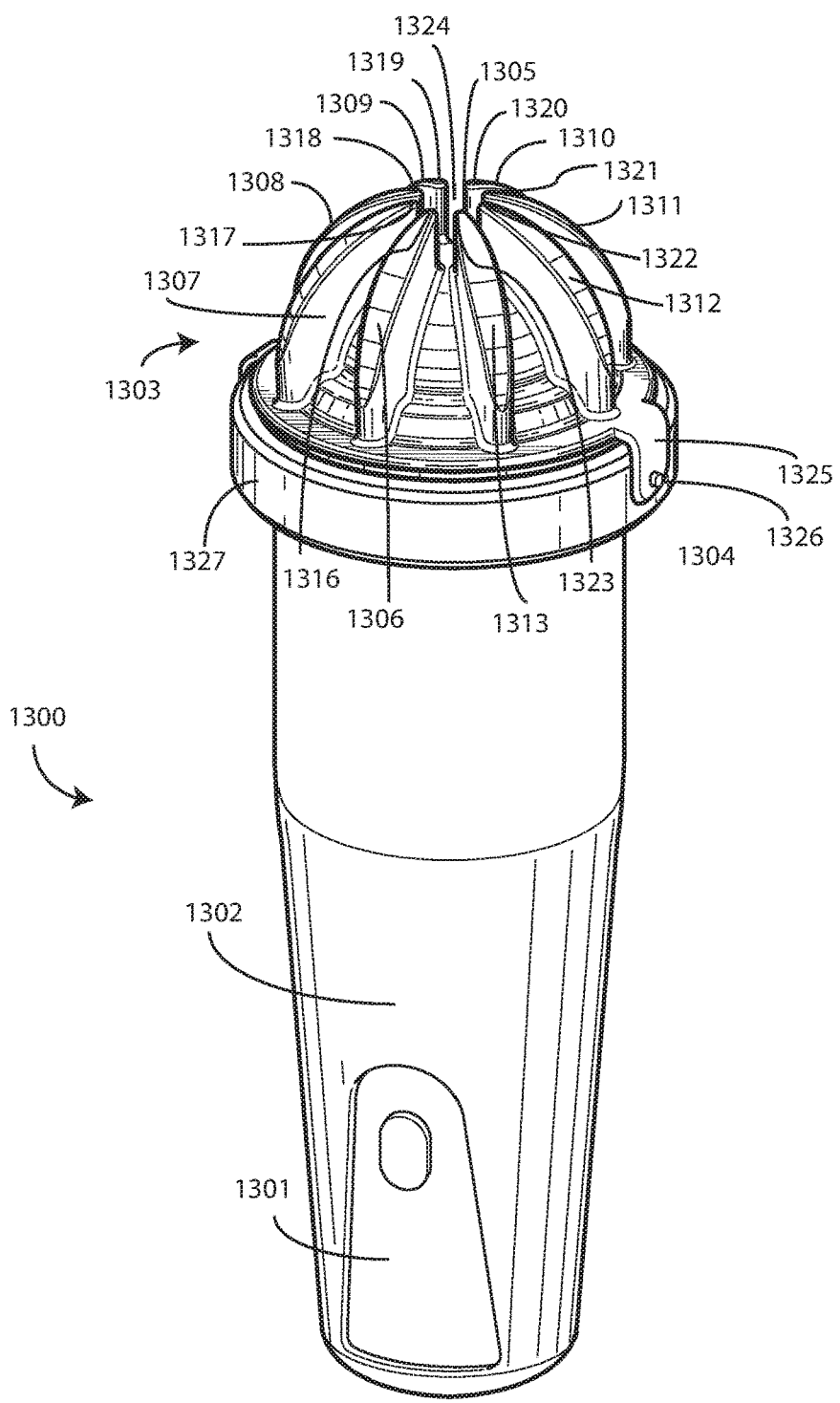
FIG. 13 illustrates another explanatory cover in accordance with one or more embodiments of the disclosure.

Turning now to FIG. 13, illustrated therein is another protective cover 1300 for a device 1301. In one embodiment, the device 1301 is a medical device. In the illustrative embodiment of FIG. 13, the protective cover 1300 includes a body 1302 and a cover 1303.

In one embodiment, the cover 1303 comprises a base member 1304 and a vault 1305 spanning an interior region of the base member 1304. As with the cap (100) of FIGS. 1-6, in this illustrative embodiment the vault 1305 comprises a plurality of partial arch trusses 1306,1307,1308,1309, 1310,1311,1312,1313 disposed along an exterior of the vault 1305. In this illustrative embodiment, each partial arch truss of the plurality of partial arch trusses 1306,1307,1308,1309, 1310,1311,1312,1313 extends from the base member 1304 to a distal edge 1316,1317,1318,1319,1320,1321,1322, 1323. The distal edges 1316,1317,1318,1319,1320,1321, 1322,1323 of the plurality of partial arch trusses 1306,1307, 1308,1309,1310,1311,1312,1313 then collectively define an interstice 1324 at an apex of the vault 1305.

The cover 1303 of FIG. 13 differs from the cap (100) of FIGS. 1-6 in that it does not include a tab (112) or tether extending from the base member 1304 about the body 1302. Instead, the cover 1303 includes a first coupler 1325 and a second coupler (disposed behind the protective cover 1300). Each attaches to a boss 1326 to retain the cover 1303 to the girdle 1327 of the body 1302.

Figure 14:
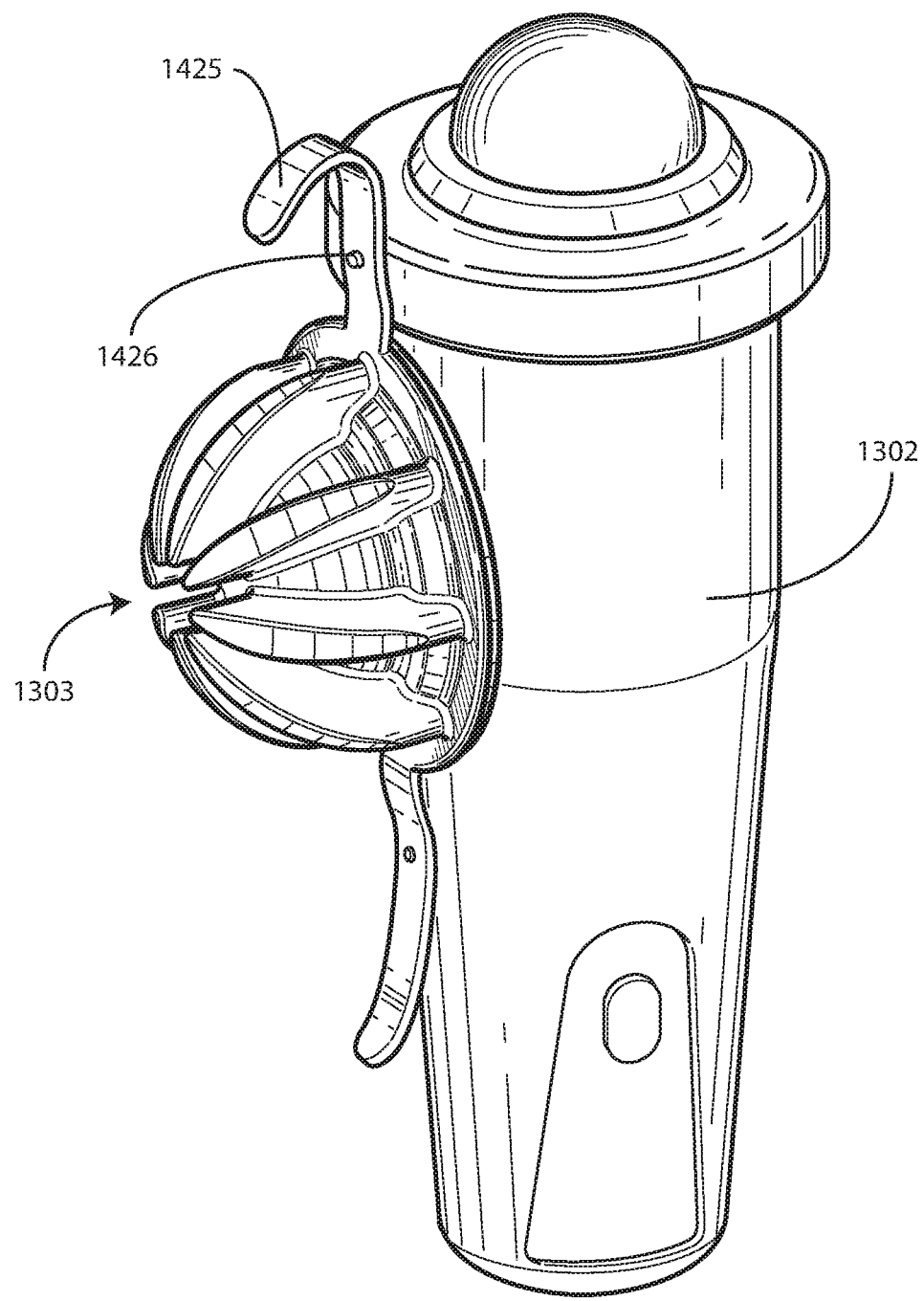
FIG. 14 illustrates another explanatory cover in accordance with one or more embodiments of the disclosure, with a cap in an open but attached configuration.

Turning to FIG. 14, the cover 1303 has been removed from the body 1302. The second boss 1426 is visible, as is the second coupler 1425. When the cover 1303 is not in use, one of the couplers, i.e., coupler 1425, can be attached to a boss 1426 to retain the cover 1303 to the body 1302.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A cover for a medical device, the cover comprising:
    a body; and
    a cap, selectively attachable to the body, the cap, comprising:
        an annulus;
        a rounded vault spanning an interior portion of the annulus, the rounded vault defining a convex exterior; and
        a plurality of partial arch trusses, each partial arch truss extending from the annulus along the convex exterior toward an apex of the convex exterior to a distal end at termination point, where a plurality of distal ends of the plurality of partial arch trusses defines an interstice at the apex.

2. The cover of claim 1, the cap further comprising a tab extending distally from the annulus.

3. The cover of claim 2, the tab terminating at an annular disc defining an aperture concentrically located along the annular disc.

4. The cover of claim 2, the body defined by a body height, the tab extending distally from the annulus by a distance greater than the body height.

5. The cover of claim 4, the cap further comprising a body coupler extending distally from the annulus on a side of the annulus opposite the tab.

6. The cover of claim 5, the body coupler defining an aperture, the body defining a boss to engage the aperture to retain the cap in an attached configuration to the body.

7. The cover of claim 1, the each partial arch truss defining a teardrop having a teardrop point disposed at the termination point and a teardrop base disposed adjacent to the annulus.

8. The cover of claim 1, the plurality of partial arch trusses comprising at least six partial arch trusses.

9. The cover of claim 8, the plurality of partial arch trusses comprising eight partial arch trusses.

10. The cover of claim 8, the cap further comprising a stair-step protuberance disposed at an intersection of the rounded vault and the annulus.

11. The cover of claim 1, the body comprising:
    a base member; and
    a round sidewall extending distally from the base member to a girdle;
    the girdle defining an aperture to receive a medical device.

12. The cover of claim 11, the round sidewall extending outward from the base member to a waist and inward from the waist to the girdle to define a double-opposing frusto-conical housing.

13. The cover of claim 12, the round sidewall defining an opening between the base member and the waist.

14. The cover of claim 13, the opening comprising an arched opening.

15. The cover of claim 12, the base member defining an aperture concentrically aligned with a central axis of the body.

16. The cover of claim 12, the round sidewall defining a concave engagement region between the waist and the girdle.

17. The cover of claim 12, the girdle having a width that is greater than a diameter of the annulus.

18. A protective cover for a device, comprising:
   a body; and
   a cover, the cover comprising:
      a base member; and
      a vault spanning an interior region of the base member, the vault comprising a plurality of partial arch trusses disposed along an exterior of the vault, and which extend from the base member to a distal edge, wherein distal edges of the plurality of partial arch trusses define an interstice at an apex of the vault.

19. The protective cover of claim 18, the cover further comprising a tether extending distally from the base member along a plane defined by the base member to engagement loop at a distal end of the tether.

20. The protective cover of claim 19, the cover manufactured from a pliant impact-absorbing polymer.

* * * * *